United States Patent [19]
Inglis et al.

[11] Patent Number: 5,756,667
[45] Date of Patent: May 26, 1998

[54] METHOD FOR PREPARATION OF AMINO ACID THIOHYDANTOINS

[75] Inventors: Adam Inglis, Strathmore; Albert Peng Sheng Tseng, Epping; Peter Laurence Adams, Mosman, all of Australia

[73] Assignee: Garvan Institute of Medical Research, Darlinghurst, Australia

[21] Appl. No.: 307,687

[22] PCT Filed: Mar. 25, 1993

[86] PCT No.: PCT/AU93/00126

§ 371 Date: Sep. 23, 1994

§ 102(e) Date: Sep. 23, 1994

[87] PCT Pub. No.: WO93/19082

PCT Pub. Date: Sep. 30, 1993

[30] Foreign Application Priority Data

Mar. 25, 1992 [AU] Australia ............... PL 1520
Sep. 17, 1992 [AU] Australia ............... PL 4798

[51] Int. Cl.⁶ ................ C07K 1/107; C07D 233/72
[52] U.S. Cl. ................ 500/345; 530/402; 514/389
[58] Field of Search ................ 530/345, 402; 514/389

[56] References Cited

U.S. PATENT DOCUMENTS 5,049,507  9/1991  Hawke .................. 436/89
5,180,807  1/1993  Bailey et al.

FOREIGN PATENT DOCUMENTS 537981  10/1992  European Pat. Off.

OTHER PUBLICATIONS

The Merck Index, p. 1336, abstract No. 9168, 1983.
Kubo et al., Chem. Pharm. Bull, 19:1, 1971, pp. 210–211.
Inglis et al., Methods in Protein Sequence Analysis (1989), pp. 137–144.
Inglis et al., Mod. Meth. in Protein and Nucleic Acid Res. (1990), 187–211.
Bailey et al., Prot. Sci 1 (1992), pp. 68–80.
Bailey et al., Biochemistry, 29:12 (1990), pp. 3145–3156.
Stark, Biochemistry, 7:5 (1968), pp. 1796–1807.
Inglis, J. Biochem. Biophys. Methods, 25 (1992), pp. 163–171.
Inglis et al., J. Biochem. Biophys Methods, 15 (1988), pp. 249–254.
Inglis, Anal. Biochem., 195 (1991), pp. 183–196.
Dwulet et al., Int. J. Pept. Protein Res., 13 (1979), pp. 122–129.
Stark, Methods in Enzymology, 25 (1972), pp. 369–384.
Meuth et al., Biochemistry, 21:16 (1982), pp. 3750–3757.
Hawke et al., Techniques in Protein Chemistry II (Pap. Annv. Symp. Protein Soc.) 4th 1990 (Pub 1991), pp. 107–114.
Goto et al., Chemical Abstract, 117: 229357d (Pub 1992).
Inglis, A.S.,Moritz, R.L., Begg, G.S., Reid, G.E., Simpson, R.J., Graffunder, H., Matschull, L., and Wittmann–Liebold, B. (1991) Methods in Protein Sequence Analysis (Jornvall, H., Hoog, J.O., and Gustavsson, A.M., Ed.), pp. 23–34. Birkhausen Verlag, Base, Dec. 1991.

Primary Examiner—Cecilia J. Tsang
Assistant Examiner—Anish Gupta
Attorney, Agent, or Firm—Rothwell, Figg, Ernst & Kurz

[57] ABSTRACT

The present invention consists in a method of preparing amino thiohydantoins either in isolation or as the C-terminals residue of a peptide. The method comprises reacting the amino acid or peptide with an acylating agent and thiocyanate or isothiocyanates in the presence of a strong acid. The present invention also relates to an improved method for C-terminal sequencing of peptides which routinely analyses all of the common amino acids of peptides. The invention involves the use of a strong, volatile, anhydrous organic or mineral acid to cleave the terminal amino acid thiohydantoin.

8 Claims, 9 Drawing Sheets

FIG. 9

METHOD FOR PREPARATION OF AMINO ACID THIOHYDANTOINS

FIELD OF THE INVENTION

The present invention consists in a method of preparing amino acid thiohydantoins either in isolation or as the C-terminal residue of a peptide. The method of the present invention is particularly useful in the preparation of proline thiohydantoins. The present invention also relates to an improved method of C-terminal peptide sequencing involving the preparation and cleavage of amino acid thiohydantoins.

BACKGROUND OF THE INVENTION

The search for a chemical method for step wise removal of amino acids from the C-terminal end of proteins began early in this century when Schlack and Kumpf (Hoppe-Seyler's Z. Physiol. Chem. 154: 125, 1926) applied the method of Johnson and Nicolet (J. Am. Chem. Soc. 33: 1973, 1911), for conversion of acylamino acids to acylthiohydantoins, to a small peptide, and then cleaved the thiohydantoins from the molecule with 1M sodium hydroxide. While alternative chemistries have been proposed over the years scientists have periodically attempted to utilize or modify the Schlack and Kumpf degradation procedure for C-terminal sequence analysis. None of the procedures proposed have, however, led to an accepted routine determination.

It has been recognised that the major hurdle to clear before full rewards can be obtained from application of the thiohydantoin procedure is the difficulty in producing prolyl residues.

Currently workers in the field are using different reagents to form thiohydantoins of amino acids. None of them have claimed to be successful with these reagents for proline. Earlier workers, Kubo et al. (Chem. Pharm. Bull. 19: 210, 1971), claim that acetyl proline and proline in two peptides reacted well at 30° with a two step reaction consisting of acetyl chloride-trifluoroacetic acid treatment, then addition of thiocyanic acid dissolved in dioxane. Unfortunately, this procedure is not a good practical solution, partly because of difficulties in preparing and storing the thiocyanic acid and it has not been elaborated by others in the field.

Earlier papers by the present inventors have reported the successful application of a thiohydantoin procedure to both manual and automatic C-terminal sequence analysis of peptides and proteins. With the exception of proline, all amino acids that might have been expected to give difficulties were shown to be degraded normally in peptides (Inglis et al In: Methods in Protein Sequence Analysis. Ed. Wittman-Liebold, 1989; Inglis et al In: Modern Methods in Protein and Nucleic Acid Research. Ed. Tschesche, 1990) These findings have been largely corroborated by others (Bailey et al J. Prot. Sci. 1:68, 1992) using different reaction conditions, despite some initial problems with amino acids such as aspartic acid, asparagine and glutamic acid (Bailey and Shively Biochemistry 29:3145, 1990). Apparently dithiothreitol (DTT) in the cleavage reagent caused adverse effects. The analysis of proline is now the major obstacle to a general routine method employing ammonium thiocyanate as the coupling reagent.

Stark (Biochemistry 7:1796, 1968) believed that the thiohydantoin procedure would not work for proline and aspartic acid. While that has now been disproved for the latter (Inglis et al In: Methods in Protein Sequence Analysis. Ed. Wittman-Liebold, 1989), it is clear from recent work that the former is quite unreactive under some circumstances and, indeed, the premise has again been advanced that the chemical pathway is such as to preclude the reaction of thiocyanate reagents with proline (Bailey et al J. Prot. Sci. 1:68, 1992). On the other hand, Kubo et al (Chem. Pharm. Bull. 19:210, 1971) obtained a product from acetylproline on which they did elemental, UV, IR and TLC analyses, all of which indicated that it was a pure sample of proline thiohydantoin. The present inventors initial findings with HSCN and acetylproline (Inglis et al In: Methods in Protein Sequence Analysis, Ed. Wittman-Liebold, 1989) were completely consistent with their results in that the present inventors also obtained a major product with an absorption maximum at 266 nm; moreover, its elution time on reversed phase columns, as compared with those of other amino acid thiohydantoins, were as expected. As far as is reported, neither Stark (Biochemistry 7:1796, 1968) nor Bailey et al (J. Prot. Sci. 1:68, 1992) tried HSCN for this purpose.

The present inventors have recently found that thiohydantoins can be made beginning with ammonium thiocyanate (Inglis et al J. Biochem. Biophys. Methods 1992). This approach followed earlier work in which thiocyanic acid was prepared in situ by adding trifluoroacetic acid to a solution of ammonium thiocyanate, acetic acid and acetic anhydride (Inglis et al In: Methods in Protein Sequence Analysis, ed. Jornvall et al, 1991). The aim in that work was to eliminate the need to chill HSCN in acetone during automatic C-terminal sequencing.

The present inventors have now been successful in producing proline thiohydantoin using a straightforward method involving reaction of acetyl proline with ammonium thiocyanate. This method is suitable for preparing other amino acid thiohydantoins and is believed to have application not only as a means for preparing standard amino acid thiohydantoins for C-terminal amino acid identifications, but also as the first reaction of a viable C-terminal sequencing procedure.

The present inventors have made the surprising discovery that the C-terminal residues of peptides can be readily cleaved using a strong volatile anhydrous organic or mineral acid thereby facilitating proline cleavage and bringing the methodology closer the the current N-terminal sequencing procedures.

SUMMARY OF THE INVENTION

Accordingly, in a first aspect the present invention consists in a method of preparing amino acid thiohydantoins either in isolation or as the C-terminal residue of a peptide comprising reacting the amino acid or peptide with an acylating agent and thiocyanate or isothiocyanate in the presence of a strong acid.

In a preferred embodiment of the present invention the amino acid or C-terminal residue of the peptide is proline.

In a preferred embodiment of the present invention the strong acid is trifluoroacetic acid.

In a preferred embodiment of the present invention the acylating agent is acetic anhydride in acetic acid.

In a preferred embodiment of the present invention the amino acid or peptide is reacted with ammonium thiocyanate, acetic anhydride in acetic acid in the presence of trifluoroacetic acid.

It is, however, presently believed that other acylating agents such as acetyl chloride for example could be used in the method of the present invention. Similarly, other strong acids beside trifluoroacetic acid such as organic fluoroacids, methanesulphonic acid, sulphuric acid, phosphoric acid, hydrochloric acid, heptafluorobutyric acid would be expected to be effective catalysts. Examples of other thiocyanate and isothiocyanate reagents which may be used in the method of the present invention include other inorganic salts such as sodium thiocyanate, polar isothiocyanates such as guanidine isothiocyanate and possibly trimethylsilyl-, phosphoryl- or benzoyl-isothiocyanate.

In a second aspect the present invention consists in an improved method of C-terminal peptide sequencing involving the production of amino acid thiohydantoins, comprising preparing the C-terminal amino acid thiohydantoin by reacting the peptide with an acylating agent and thiocyanate or isothiocyanate in the presence of a strong acid and cleaving the C-terminal amino acid with a volatile, anhydrous, organic or mineral acid.

In a preferred embodiment of the present invention the amino acid or peptide is reacted with ammonium thiocyanate, acetic anhydride in acetic acid in the presence of trifluoroacetic acid and cleaved with a volatile, anhydrous, organic or mineral acid.

In a preferred embodiment of the present invention the cleavage of the C-terminal residue is achieved using anhydrous hydrochloric acid in acetic acid.

In a preferred embodiment of the present invention the cleavage of the C-terminal residue is achieved using hydrochloric acid vapour.

In a preferred embodiment of the present invention the amino acid or C-terminal residue of the peptide is proline.

It is, however, presently believed that other acylating agents such as acetyl chloride for example, could be used in the improved method of the present invention. Similarly, other strong acids besides trifluoroacitic acid, such as organic fluoroacids, methanesulphonic acid, sulphuric acid, phosphoric acid, hydrochloric acid, heptafluorobutyric acid would be expected to be effective catalysts. Examples of other thiocyanate and isothiocyanate reagents which may be used in the method of the present invention include other inorganic salts such as sodium thiocyanate, polar isothiocyanates such as guanidine isothiocyanate and possibly trimethylsilyl-, phosphoryl- or benzoyl-isothiocyanate.

In a preferred embodiment of the present invention, the peptide is reacted with ammonium thiocyanate and acidic anhydride in acetic acid in the presence of trifluoroacetic acid, and the C-terminal amino acid thiohydantoin is cleaved with anhydrous hydrochloric acid in acetic acid or hydrochloric acid vapour.

In order that the nature of the present invention may be more clearly understood preferred forms thereof will now be described with reference to the following example and figures in which:

DESCRIPTION OF THE DRAWINGS

FIGS 1a–1d HPLC chromatograms of products from reaction of acetylproline and ammonium thiocyanate. FIGS. 1(a) and 1(b) were obtained after reaction temperatures of 40° C. and 80° C. respectively, and indicate that the yield of P is increased by 50% at the higher temperature.

FIGS. 3a and 3b HPLC analyses of HC1 of hydrolysis products of the purified peak P. (a), and a standard amino acid mixture, (b), after derivatization with PITC, showing that P was converted to PTC-proline. α-Aminobutyric acid (AB) was added as an internal standard.

FIGS. 5a and 5b Postulated reactions involved in the formation of proline thiohydantoin from a mixture of acetylproline, acetic anhydride, acetic acid, trifluoroacetic acid and ammonium thiocyanate. FIG. 5(b) rationalises the formation of Pro-TH from the isothiocyanate of acetyl proline.

FIGS. 7(a.1, a.2, b.1, b.2, c.1, c.2, c.3 and c.4) Results of degradation cycles on TyrPhe (a) and Met-enkephalin ( . . . FM) (b), and neuromedin N ( . . . PYIL) (c) without extractions and with anhydrous acid cleavage.

FIG. 8 Effect of anhydrous cleavage on proline analysis. The figure shows two degradation cycles of the tripeptide. Pyr-Leu-ProNH$_2$ after deamidation. Pro-TH elutes with background, Leu-TH is in the second cycle, not in the first.

Material and Equipment

Acetylproline (Sigma Chemical Co.); ammonium thiocyanate (BDH, Analar), Aristar acetic acid (BDH), eptide synthesis grades of trifluoroacetic acid and acetic anhydride (Applied Biosystems) were used without further purification. Reagents for amino acid analysis of phenylthiocarbamyl amino acids were all of the highest possible purity (Inglis et al Biochem. Biophys. Methods 15:249, 1988). Pierce 6M constant boiling HCl and Analar phenol (BDH) were used for hydrolysis and N,N-diisopropylethylamine (DIEA, Peptide Synthesis Grade, Applied Biosystems) replaced triethylamine in the drying reagent and in the coupling buffer.

The preparative HPLC consisted of a 140A Solvent Delivery System (Applied Biosystems), a Waters U6K Injector, an RP-300, C8, 7 µm, 4.6×220 mm reversed-phase column, a Waters 490 Programmable Multiwavelength Detector, a Waters 990 Diode Array Detector and a SE20 BBC Goerz Metrawatt Printer.

Amino acid analysis was made on a Waters 500 system equipped with a Wisp autosampler, a 3.9×300 mm Pico-Tag column and a 490 detector.

Methodology

Figure 1A:
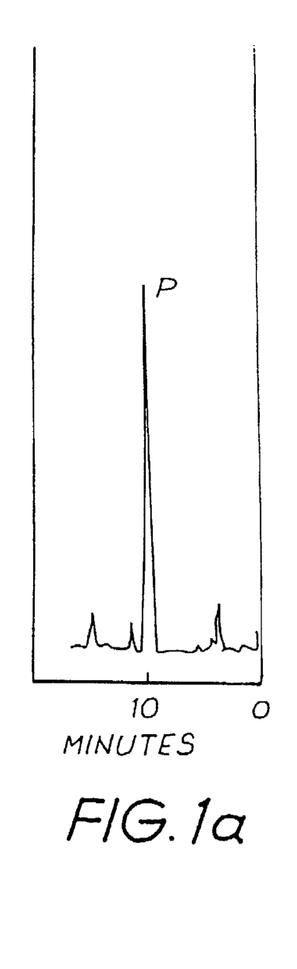
Figure 1B:
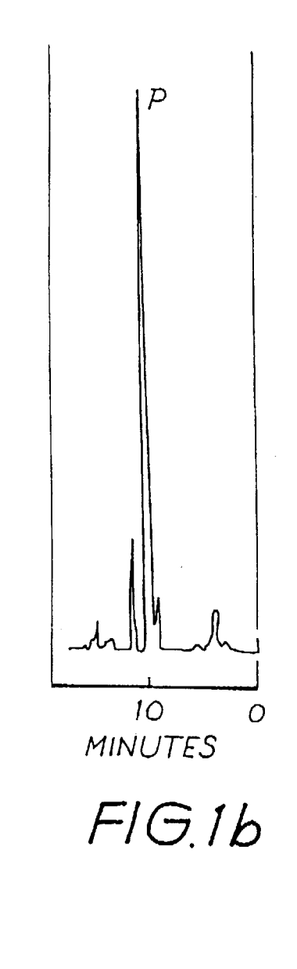
Figure 1C:
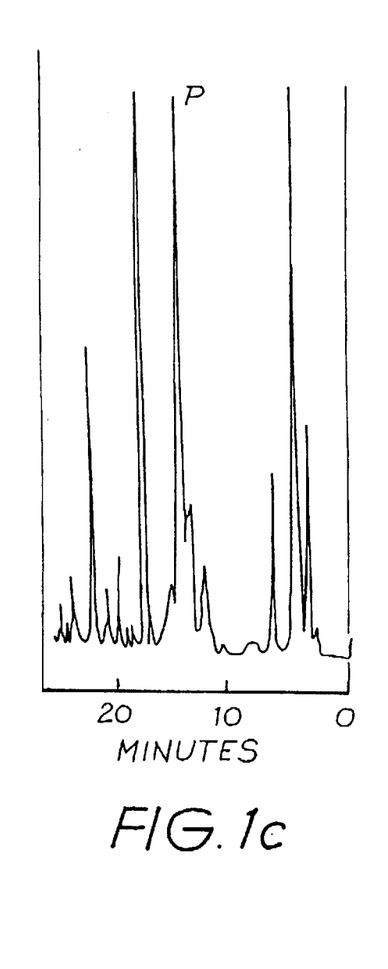
FIG. 1(c) shows a trace of portion of the preparative mixture which was fractionated to give a highly enriched peak P, as indicated in FIG. 1(d).
Figure 1D:
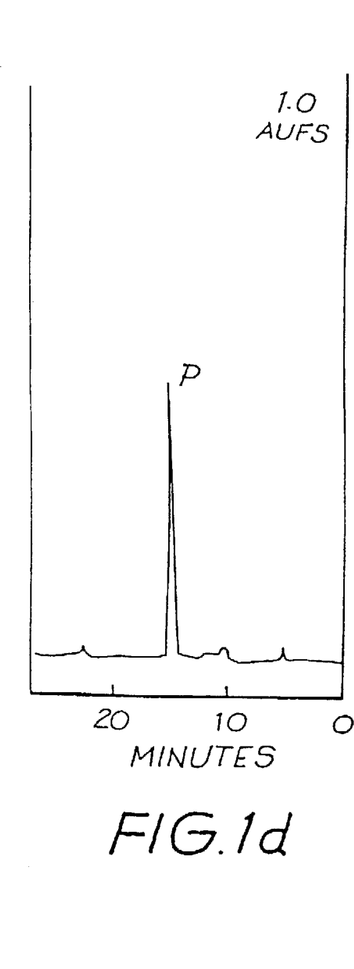

Preparation of proline thiohydantoin. Acetylproline (1 mg) was weighed in a polypropylene Eppendorf tube (1.5 ml), ammonium thiocyanate (30 mg), acetic anhydride (1 ml), acetic acid (200 µl) and trifluoroacetic acid (100 µl) were added and the tube was sealed with the screw cap. The tube was vortexed to accelerate solution of the thiocyanate and the contents were heated to 80° C. for 30 min. After cooling, the contents were transferred to a polypropylene conical tube (10 ml), shell frozen in liquid nitrogen and freeze dried overnight. The Pro-TH was separated from excess reagents and reaction by-products by gradient HPLC on an Aquapore reversed-phase column using a peptide buffer system (0.1% TFA in water-buffer A, 0.1% TFA and 60% acetonitrile in water-buffer B) at a flow of 1 ml/min. The chromatograms shown for comparison of the yields after different reaction temperatures (FIGS. 1(a) and 1(b) were obtained with a linear gradient from 0% A to 35% B over 35 min. For these analytical runs, the dried samples were dissolved in 10% acetonitrile (1 ml), 50 µl was diluted further to 1 ml, and 100 µl was injected into the HPLC. The gradient program for the preparative run consisted of an isocratic step of 7 min with buffer A followed by a linear change to 35% B over 33 min. No reductant was added to the buffers (Inglis Anal. Biochem. 195:183, 1991). This approach gave a product which was free from inorganic salts and was suitable for direct mass spectrometric analysis. The eluate was monitored at 266 nm. Unreacted acetylproline (detected at 220 nm) was eluted approximately 4 min before Pro-TH. For preparative runs the instrument was desensitized by monitoring at 235 nm and fractions were collected across the peak P. The fractions were freeze dried overnight. Samples were taken for mass spectometry, amino acid analysis and UV spectra.

Mass spectrometry. The sample was taken in dryness under vacuum and transferred to a probe cup for direct analysis. The 70 eV probe electron impact (EI) spectra were obtained with a VG Autospec-Q mass spectrometer (VG Analytical Ltd., Manchester, UK) operating at an accelerating potential of 8 kV, and with a mass resolution of at least 5,000 (10% valley definition). Results reported are the average of at least five magnet scans across the mass range m/z 500-50 at a scan rate of 5 secs per decade. Data were acquired in the centroid mode and then mass measured against pentafluorokerosene (PKF) which was introduced along with the sample.

Amino acid analysis. PTC-amino acid analyses were carried out as previously described [Inglis et al J Biochem. Biophys. Methods 15, 249-254, 1988) with the following exceptions. The reacti-vial was connected directly to the cold trap of the vacuum pump for both sample dryings and vacuum sealing. This was found to be more effective than evacuating via the Pico-Tag Work Station. The screw top of the reacti-vial was covered with a thin layer of Teflon tape and additional HCl (total=400 µl, containing 0.5 mg phenol) was added to the vial to compensate for loss of HCl during removal of oxygen from the vial. Evacuation for vapour phase hydrolysis consisted of three short stages; the first two were of only a few seconds duration as the valve was opened cautiously and shut to de-gas the acid, the third stage was of approximately 25 secs duration with full vacuum to thoroughly evacuate the flask. The samples were hydrolysed for 1–4 hr at 150° C. in the presence of α-aminobutyric acid as an internal standard. After hydrolysis, the hydrolysis tubes were wiped to remove HCl from the outside and transferred to a clean reacti-vial, dried under vacuum for 5 min, then redried from DIEA-methanol (1:2, 20 µl). The amino acids were derivatized (25 min, 20° C.) with metha-nol:DIEA:PITC:water (7:1:1:1, 20 µl), diluted with 3% acetonitrile in Milli-Q water (80 µl) and transferred to the Wisp limited volume inserts containing heptane (40 µl). The tubes were vortexed briefly to ensure that the excess PITC was extracted by the heptane, centrifuged (14,000 rpm, 30 sec) to clarify the aqueous solution then transferred to the Wisp containers for analysis in the usual way by HPLC.

EXAMPLE 1

FORMATION OF PROLINE THIOHYDANTOIN

Considering the difficulties encountered with some procedures in obtaining a sample of proline thiohydantoin (Bailey and Shively Biochemistry 29:3145, 1990), the preparation of the compound with our procedure was remarkably easy (Inglis et al J. Biochem. Biophys. Methods 1992). In this work the inventors dispensed with the initial treatment of the acetylproline with an acetic acid-acetic anhydride mixture. Since ammonium thiocyanate is soluble in acetic acid the inventors also left out the acetone that was originally required for preparation of the thiocyanic acid. It is clear from FIG. 1a that even reaction at 40° for 30 min. gave a reasonable yield of proline thiohydantoin (P). Although higher temperatures gave increased yields, more background products were evident.

FIG. 1 shows analytical chromatograms obtained after HPLC of reaction mixtures containing acetylproline and ammonium thiocyanate. The peak P (Pro-TH) is FIG. 1(a) is much smaller after reaction at 40° C. as compared with an 80° C. reaction (FIG. (b)), which is consistent with a higher yield of Pro-TH at the higher temperature. The yield of Pro-TH, based on the peak height at 80° C. and comparison with the peak height of a pure sample of Phe-TH, was approximately 70%. Because there was little evidence for any acetylproline remaining, and the reactions were not conducted in an inert atmosphere so some of the thiohydantoin may also have decomposed, this result is encouraging from a sequencing standpoint. The temperature of 80° C. was chosen based on earlier results (Inglis et al In: Methods in Protein Sequence Analysis Ed. Wittman-Liebold, 1989) on amino acids such as leucine. However, it is also clear that the product obtained at 40° is much cleaner than that at 80°, which suggests that there is further scope for improvement in the reaction conditions. The thiohydantoins of valine and methionine are eluted also in this portion of the chromatogram (data not shown). The phenylthiohydantoins of valine, methionine and proline are eluted close together on reversed-phase columns, so one might expect that their thiohydantoins would also be eluted in the same region of the chromatogram. The elution time for P is consistent with this argument. FIG. 1(c) is a trace of portion of the preparation before purification, and FIG. 1(d) is an analytical run on P after fractionation of these products. This highly purified material was further analyzed by mass spectrometry and amino acid analysis.

Figure 2:
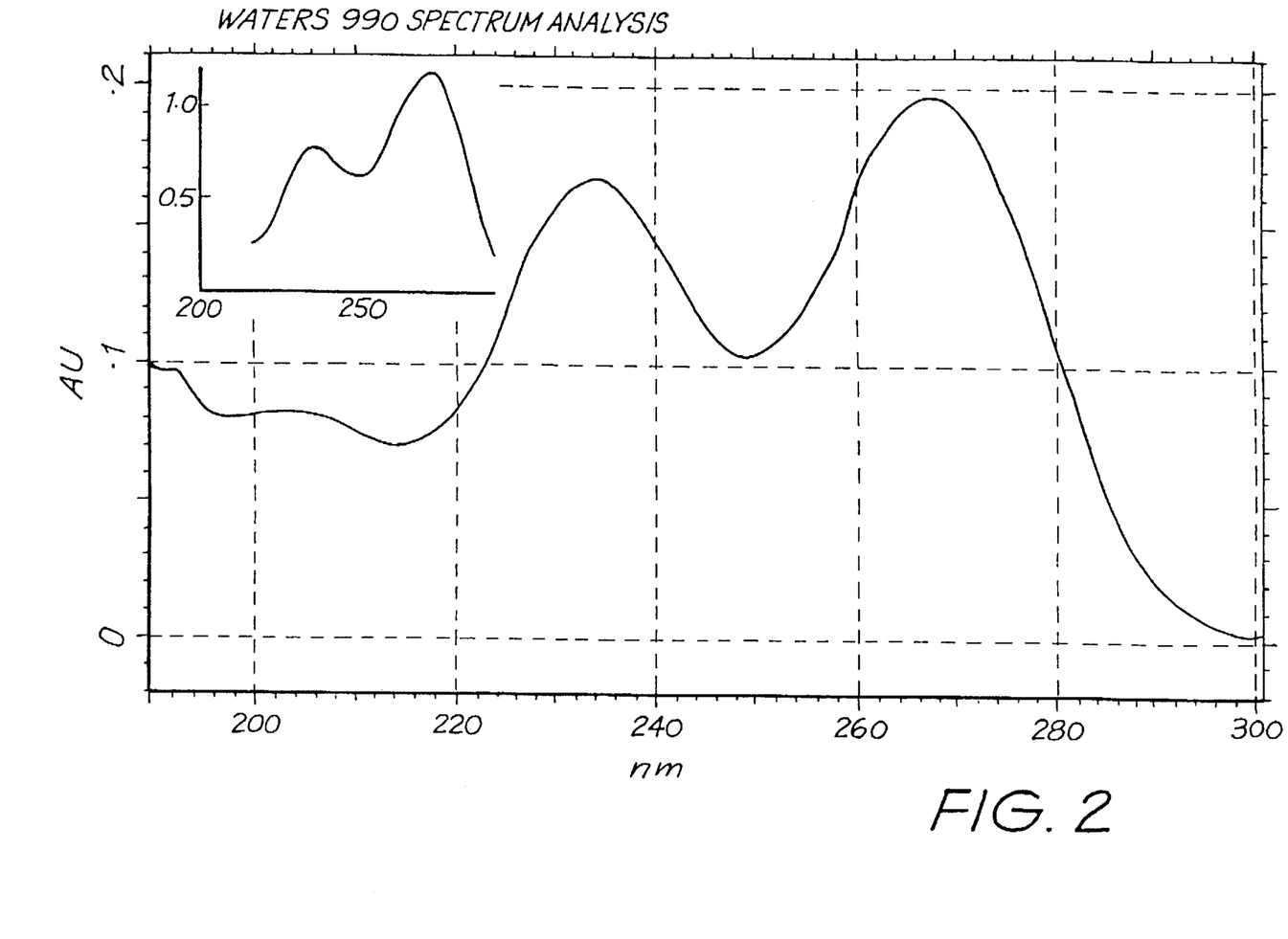
FIG. 2 Comparison of the UV spectrum of the purified peak P as obtained from a diode array detector during the analytical run (FIG. 1(d)) with that previously found (Kubo et al Chem. Pharm. Bull. 19:210, 1971) for Pro-TH in ethanol (insert). The curves show some differences in the shorter UV region where the HPLC solvent will provide additional absorption, but both exhibit a minimum at 250 nm and a maximum near 266 nm that is characteristic of thiohydantoins.

The UV absorption spectrum of purified P (FIG. 2) was obtained during HPLC (in acetonitrile-water-TFA) with a diode array detector. Bearing in mind the different solvent systems, which would probably account for a higher absorption of the HPLC product in the short UV, the similarities to the spectrum originally published by Kubo et al (Chem. Pharm. Bull. 19:210, 1971) of Pro-TH in ethanol are quite marked, both having a minimum at 250 nm and the characteristic absorption maximum of thiohydantoins at 267 nm. A molar extinction coefficient of approximately 18,000 was obtained for Pro-TH at this wave length, based on the yield of the phenylthiocarbamyl derivative (PTC) of proline obtained from amino acid analysis. This value is comparable to those found for other amino acid thiohydantoins.

Figure 3A:
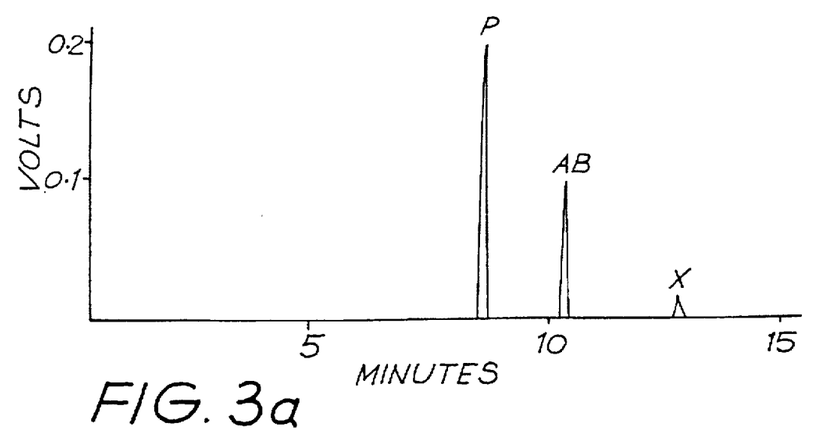
Figure 3B:
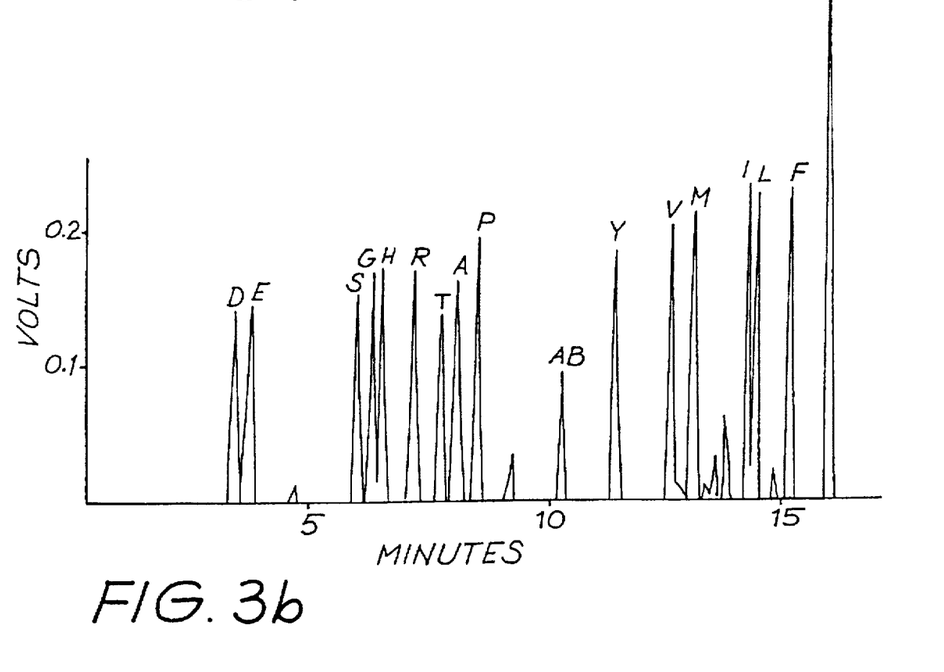

Purified P was hydrolysed with 6M HCl in the vapor phase at 150° C. for 1 h. The products were reacted with phenylisothiocyanate and separated on a reversed-phase HPLC column to ascertain whether PTC-Pro was present. In earlier work, Cromwell and Stark (Biochemistry 8:4735, 1969) used both acid (48% HBr) and base hydrolysis without success to convert thiohydantoins to amino acids, and finally succeeded with a three stage procedure involving formation of the thiohydantoic acid, oxidation with peroxide and alkaline hydrolysis. The amino acid analysis chromatogram for P (FIG. 3) showed that there are two major peaks, in the positions of PCT-proline and PTC-α-aminobutyric acid (AB, the internal standard). There was a third product (X), which was also formed when the thiohydantoins of leucine and valine were hydrolysed, near PTC-valine. Extending the hydrolysis time to 4 hours led to an increase in the yields of PTC-valine. PTC-leucine and the by-product. However, a small peak is also routinely found in that position. This back-hydrolysis procedure has not been investigated in any depth and was used primarily as an alternative means of identifying the peak P.

Figure 4:
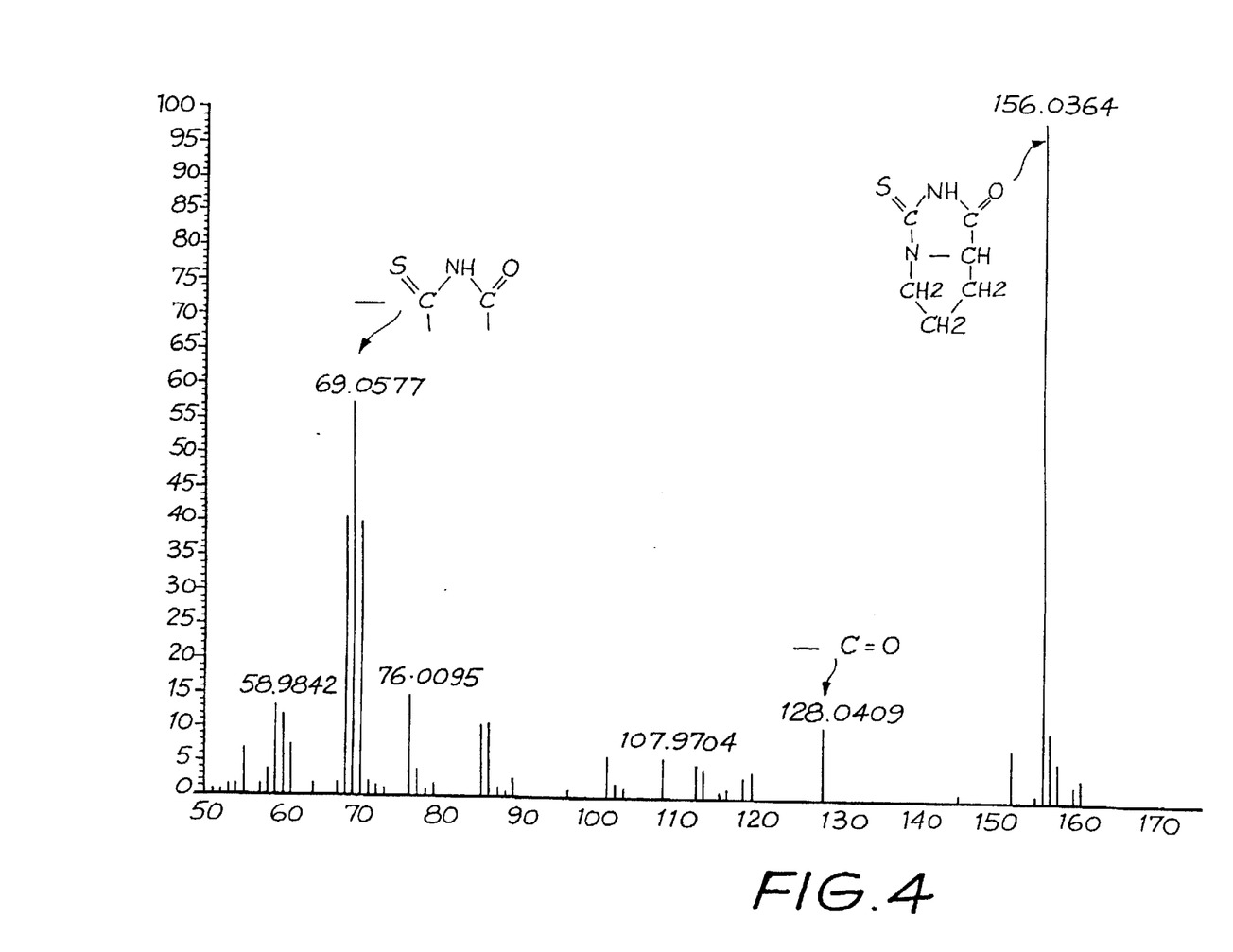
FIG. 4 Mass spectrum of peak P showing both the purity of the product and the correct elemental composition for Pro-TH. Major ions of lower molecular weight are consistent with losses of elements from the thiohydantoin ring.

Excellent supportive data for the identification of peak P as Pro-TH was obtained from mass spectroscopy (FIG. 4). The mass of the M+ ion was found to be 156.0364 au. The proposed structure, i.e. $C_6H_8N_2O_1S_1$, is consistent with this finding within an error of 017 mDa. Other diagnostic ions in the spectrum are m/z 128.0409 ($C_5H_8N_2S_1$; M-CO) and m/z 69.0577 ($C_4H_7N_1$; M-CSNHCO). For these assignments, the error between experimental data and calculated formulae was within +/-0.1 mDa (i.e., 0.1 mau).

The reaction conditions described for the preparation of Pro-TH are also suitable for preparation of other amino acid thiohydantoins (Inglis et al In: Methods in Protein Sequence Analysis, Ed. Jornvall et al, 1991). Here it will be noted that the inventors dispensed with the initial acylation with an acetic anhydride-acetic acid mixture, and added all of the reagents at the outset. Acetone, which was the solvent used for the thiocyanic acid procedure (Dwulet and Gurd Int. J. Pept. Protein Res. 13:122, 1979), was also omitted. These omissions did not appear to be detrimental. The findings confirm earlier work with thiocyanic acid (Inglis et al In: Methods in Protein Sequence Analysis Ed. Wittman-Liebold, 1989; Dwulet and Gurd Int. J. Pept. Protein Res. 13:122, 1979) and ammonium thiocyanate (Inglis et al In: Methods of Protein Sequence Analysis Ed. Jornvall et al 1991) that indicated that ammonium thiocyanate in the absence of a strong acid was not an ideal reagent. They might also provide an explanation for the failure of Bailey and Shively (Biochemistry 29:3145, 1990) to obtain a thiohydantoin of proline with ammonium thiocyanate. However, because trimethylsilyl-isothiocyanate also failed to produce a thiohydantoin with proline in their experiments, doubts must be raised also as to the efficacy of this reagent.

Figure 5A:
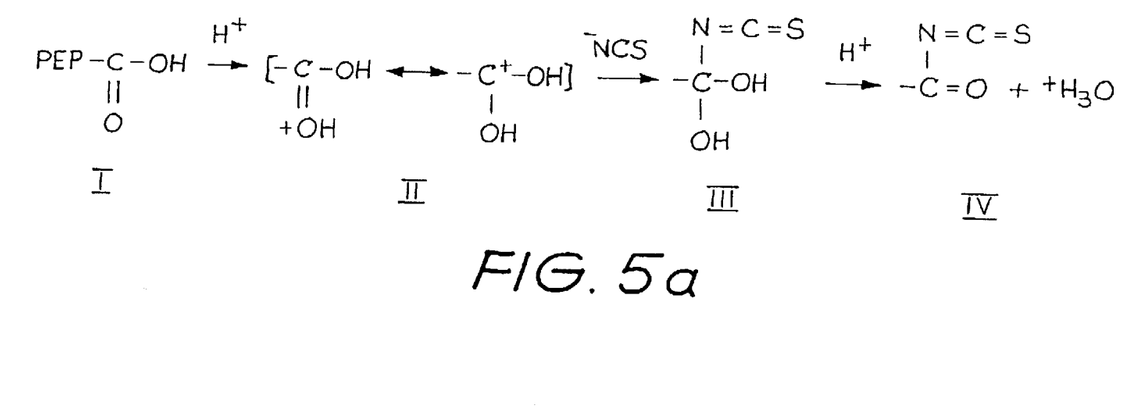
FIG. 5(a) shows a general scheme for formation of an isothiocyanate at the C-terminus of peptides based on acid-catalyzed activation of the carboxyl group.
Figure 5B:
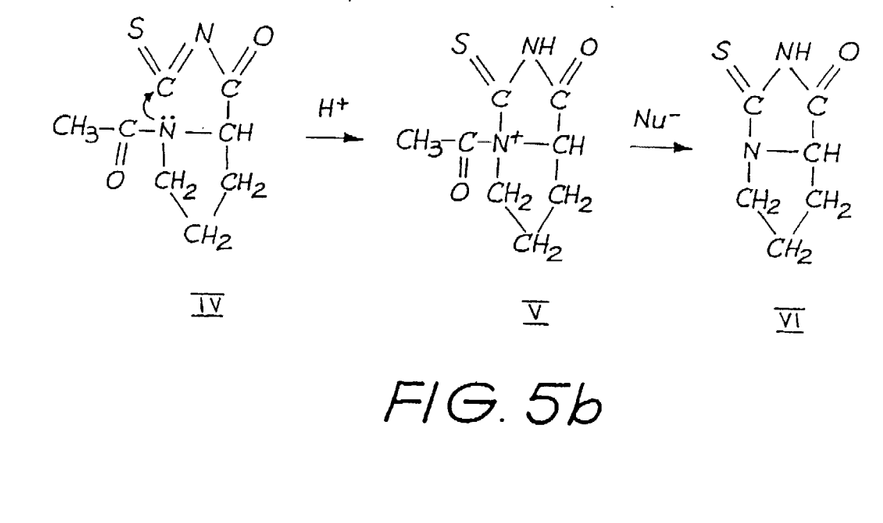
Figure 6A:
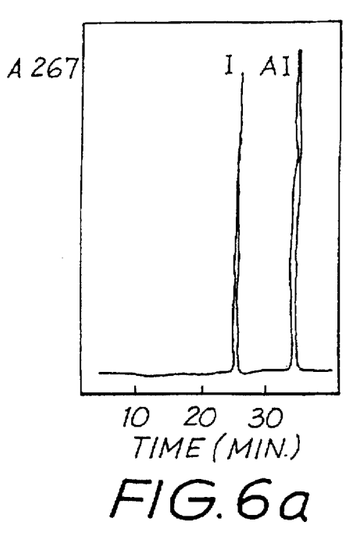
FIGS. 6a–6f Cleavage of acetyl isoleucine thiohydantoin (AI) under various acidic conditions. (a) shows the HPLC trace for pure AI and I (Ile-TH); (b) indicates that AI is stable in the coupling mixture; (c) shows partial decomposition in TFA; (d), (e) and (f) show the extent of cleavage in acetyl chloride (40 µl) containing methanol (10 µl), methanol (50 µl) and water (10 µl), respectively.
Figure 6B:
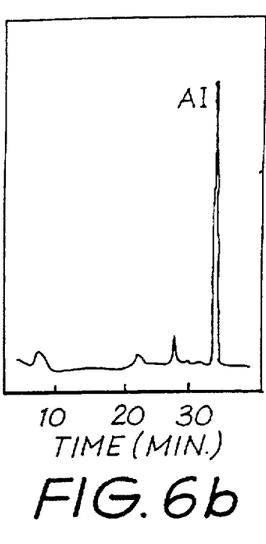
Figure 6C:
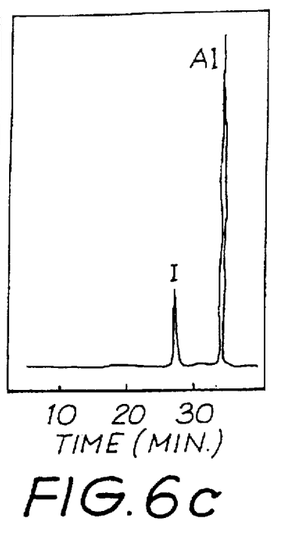
Figure 6D:
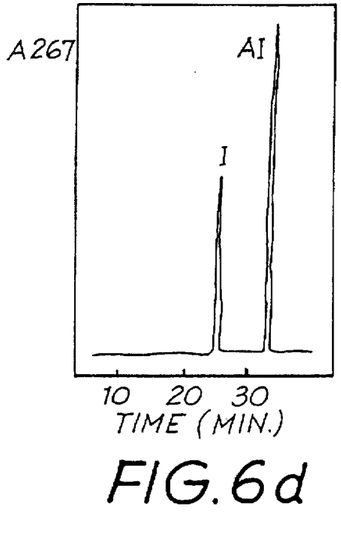
Figure 6E:
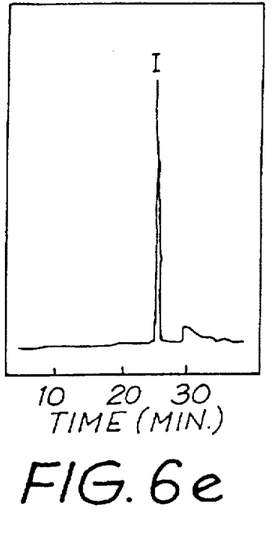
Figure 6F:
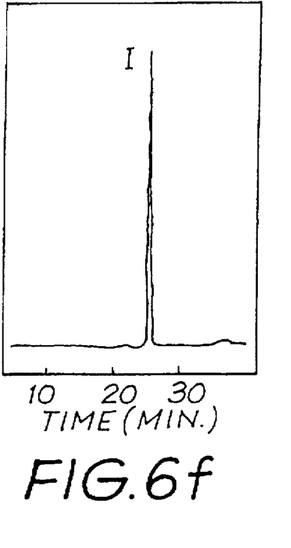
Figure 7:
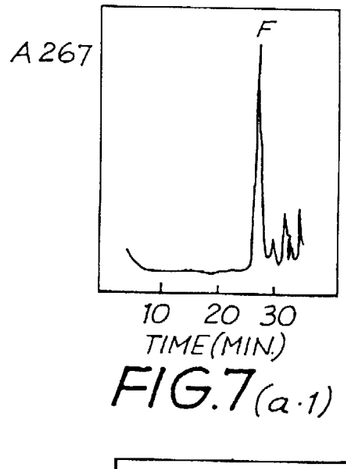

The positive results for reaction of proline with thiocyanate in the presence of a strong acid imply, firstly, that the reaction pathway does not proceed via either a mixed anhydride or an oxazolinone derivative of the carboxyl group of the C-terminal amino acid, as proposed earlier (Stark In: Methods in Enzymology 25:369, 1972) (see Inglis Anal. Biochem. 195:183, 1991) for discussion); secondly, that a plausible mechanism should invoke participation of hydrogen ions in the process. Our proposal (FIG. 5) is that the hydrogen ions of the strong acid activate the carboxyl group, rendering it more susceptible to nucleophilic attack by the isothiocyanate ion, in a manner analogous to the acid-catalyzed formation of carboxylic acid esters. The reactions shown in FIG. 5(a) are actually equilibrium reactions and formation of the peptidyl isothiocyanate (IV) is favoured by employing excess of one of the reagents, for example, the isothiocyanate. Elimination of the water molecule from III would be helped by the presence of acetic anhydride. The thiohydantoin ring may be formed as proposed (Stark In: Methods in Enzymology 25:369, 1972) by reaction of the nitrogen atom of the C-terminal amino acid with the electrophilic carbon of the isothiocyanate (IV). However, what is unique in the reaction of acetylproline with thiocyanate when compared with the reaction of other acylamino acids is that the product obtained does not contain an acetyl group (VI, FIG. 5(b)). The present work corroborates the findings of Kubo et al (Chem. Pharm. Bull. 19:210, 1971; Inglis et al In: Methods in Protein Sequence Analysis, Ed. Wittman-Liebold, 1989) with thiocyanic acid in this regard. Unlike other amino acids, the proline nitrogen is already part of a pyrrolidine ring and is devoid of a hydrogen atom for transfer on ring closure (IV, FIG. 5(a)); therefore, formation of a thiohydantoin and loss of the acetyl group implies that the expected structure V containing a quaternary nitrogen is unstable. Apparently, in V the acetyl link to the proline nitrogen is weakened and cleavage of the bond occurs in the presence of an appropriate nucleophile, leaving the more stable proline thiohydantoin (VI). As pointed out by Inglis (Anal. Biochem. 195:183, 1991), acidic conditions would be expected to favour cyclization of the peptidyl isothiocyanate and this may have particular relevance in the case of proline.

It is well-known (Inglis Anal. Biochem. 195:183, 1991) that acylated amino acids are not ideal models for studies on the thiohydantoin procedure for C-terminal sequencing because they usually react more readily than the same amino acid in a peptide chain; hence, it does not necessarily follow that the amino acid thiohydantoin will also fall off on reaction of proline in peptides. In that event it could be argued that acid conditions should be used for cleavage because alkali might cause ring opening (to IV) and not cleavage.

EXAMPLE 2

ACIDIC CLEAVAGE OF THE THIOHYDANTOIN

Stark (Biochemistry 7:1796, 1968) tried both methanolic HCl and trifluoroacetic acid (TFA) as cleavage reagents. TFA was not effective. HCl in methanol was, but it also reacted with the residual peptide and prevented a second degradation. 12M HCl was then tried with some success but it was relinquished in favour of acetohydroxamic acid. The present inventors obtained similar results to Stark for cleavage of acylamino acid thiohydantoins with either TFA or methanolic HCl. However the inventors also found that anhydrous HCl in acetic acid was superior to both of them. In these experiments (see FIG. 6) the HCl was generated in situ from reaction of water with acetyl chloride although gaseous HCl alone should suffice.

The HCl cleavage procedure was then applied successfully to tyrosylphenylalanine, Met-enkephalin and neuromedin N (see FIG. 7), hence establishing (i) that the cleavage also occurs with peptides, and (ii) that the new carboxy terminus is free for a repeat operation. To verify the principle, the experiments were carried out very simply starting with around 0.5 μM peptide, 100 μl of coupling mixture and loading approximately 30 nm of the cleaved material. Elution was made on a C18 column using peptide elution conditions. The same tube was used throughout and just dried in the Savant between the coupling and cleavage reactions. Although background remained, or built up during successive cycles, the inventors knew residues appeared at cycles 2 and 3. A small peak in the proline area also appeared in cycle 4 of neuromedin N. To confirm the assignment of these, the digests were spiked with the expected amino acid and rerun. While the conditions were not optimized, cleavage for 15 min. at 70° C. gave results similar to those obtained using base cleavage (3 min., R.T., 0.5 M KOH in 33% methanol, plus DTT). Besides establishing the effectiveness of anhydrous acid cleavage for the thiohydantoin procedure, this work also highlights the advantage of (i) having a readily removable cleavage reagent, and (ii) not having to neutralize between the two reaction steps. Samples cleaved by base, for example, gave greatly reduced yields in the second cycle. The present inventors believe, therefore, that this new approach is a major step towards the development of an automated non-covalent attachment method on insoluble supports that would be applicable to all amino acid residues in peptides.

EXAMPLE 3

CLEAVAGE AT PROLINE RESIDUES

Figure 8:
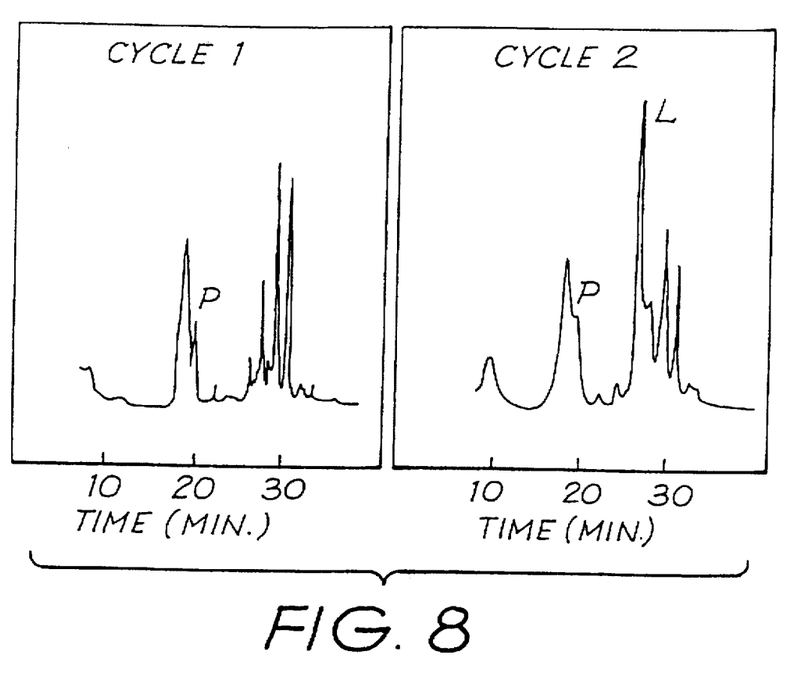

The tripeptide (PyrogluLeuProNH$_2$) was analyzed (see FIG. 8) after removal of the amide group with pH 2 formic acid (110° C., 2 h). The results confirm that proline linked to a leucine does not cleave concomitantly (as does acetylproline), but it does react. Unequivocal assignment cannot be made at Cycle 1 because of a background peak but Leu-TH is clearly seen at Cycle 2. When proline cleavage occurs it could well be sequence dependent; however, the present inventors work suggests that proline should no longer be a deterrent to the use of the thiohydantoin procedure. While other procedures might be applicable, the success of the simple approach employed here suggests that it could be readily refined, automated, etc.

The present inventors have now shown that all of the possibly intractable residues in proteins react satisfactorily in the thiohydantoin degradation procedure. Hence, there are now no major obstacles to the development of a general procedure for C-terminal sequencing.

Figure 9:
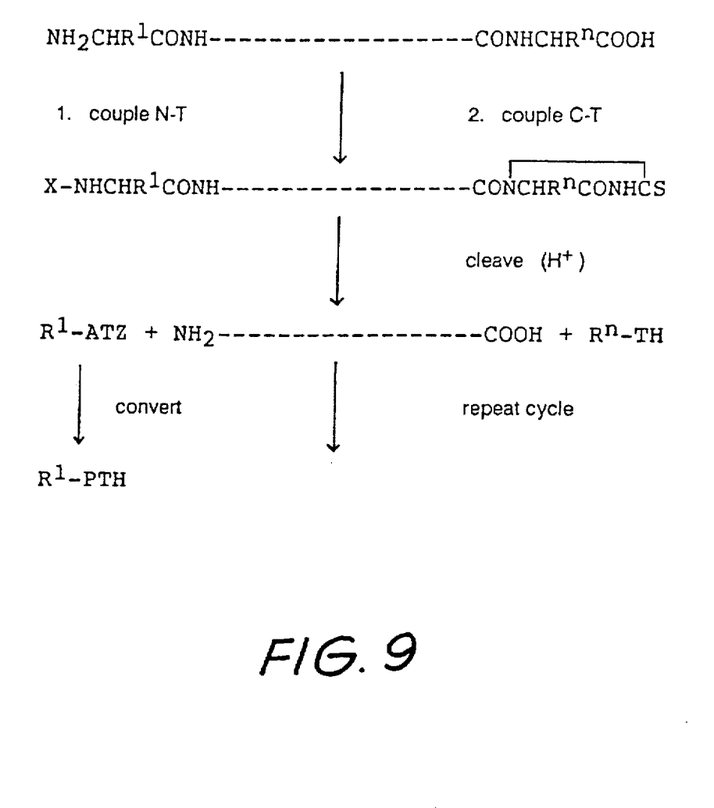
FIG. 9 Scheme for dual degradation procedure of a protein.

This work also suggests that acid cleavage is a viable alternative to basic cleavage. The aspects of the optimal strength of the acid and the extent of non-specific cleavage need to be addressed further. However, apart from virtues that the anhydrous cleavage may have for C-terminal sequencing, it could well have opened the door to a combined N- and C-terminal sequencing method for the first time. One can now conceive of a procedure in which the N- and C-terminal amino acids are derivatized in turn using Edman and thiohydantoin chemistry and then cleaved with a volatile, anhydrous organic or mineral acid (scheme in FIG. 9).

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

We claim:

1. A method of preparing proline thiohydantoins either in isolation or as the C-terminal residue of a peptide comprising reacting proline or the peptide with an acylating agent and an isothiocyanate in the presence of a strong acid, wherein said isothiocyanate is selected from the group consisting of guanidine isothiocyanate, trimethylsilyl-isothiocyanate, phosphoryl-isothiocyanate and benzoyl-isothiocyanate.

2. A method of preparing proline thiohydantoins either in isolation or as the C-terminal residue of a peptide comprising reacting proline or the peptide with an acylating agent and an isothiocyanate in the presence of a strong acid, wherein said acylating agent is acetic anhydride in acetic acid.

3. A method of preparing proline thiohydantoins either in isolation or as the C-terminal residue of a peptide comprising reacting proline or the peptide with ammonium thiocyanate and actic anhydride in acetic acid in the presence of trifluoroacetic acid.

4. A method of preparing proline thiohydantoins as the C-terminal residue of a peptide comprising reacting the peptide with an acylating agent and thiocyanate or isothiocyanate in the presence of a strong acid.

5. A method as claimed in claim 4, in which the thiocyanate is ammonium thiocyanate.

6. A method as claimed in claim 4, in which the isothiocyanate is selected from the group consisting of guanidine isothiocyanate, trimethylsilyl-isothiocyanate, phosphoryl-isothiocyanate and benzoyl-isothiocyanate.

7. A method as claimed in claim 4, in which the acetylating agent is acetic anhydride in acetic acid or acetyl chloride.

8. A method as claimed in claim 4, in which the strong acid is selected from the group consisting of an organic fluoroacid, methanesulphonic acid, sulphuric acid, phosphoric acid and hydrochloric acid.

* * * * *